United States Patent
Shimizu et al.

(12)
(10) Patent No.: US 6,179,966 B1
(45) Date of Patent: Jan. 30, 2001

(54) METHOD FOR PRODUCING ACRYLIC ACID

(75) Inventors: Toyomitsu Shimizu; Osamu Moriya; Kunihiko Shigematsu; Ryuji Matsushita, all of Niihama (JP)

(73) Assignee: Sumitomo Chemical Company, Ltd., Osaka (JP)

( * ) Notice: Under 35 U.S.C. 154(b), the term of this patent shall be extended for 0 days.

(21) Appl. No.: 09/192,517

(22) Filed: Nov. 17, 1998

(30) Foreign Application Priority Data

Nov. 17, 1997 (JP) .................................................. 9-314974

(51) Int. Cl.[7] .............................. B01D 1/00; B01D 3/36; C07C 51/46
(52) U.S. Cl. ................................ 203/15; 203/14; 203/38; 203/59; 203/DIG. 21; 159/47.1; 562/600
(58) Field of Search ................................ 203/38, 57, 69, 203/59, 8, 15, 14, 73–74, 80, 91, DIG. 21, 68, 62; 562/600, 531, 532, 545; 159/47.1

(56) References Cited

U.S. PATENT DOCUMENTS

| 3,781,193 | * | 12/1973 | Sennewald et al. | ............. | 203/52 |
| 3,844,903 | * | 10/1974 | Willersinn et al. | ......... | 203/DIG. 21 |
| 3,859,175 | | 1/1975 | Ohrui et al. | . | |
| 3,893,895 | * | 7/1975 | Dehnert et al. | .......... | 203/59 |
| 3,932,500 | * | 1/1976 | Duembgen et al. | ............. | 203/68 |
| 4,317,926 | * | 3/1982 | Sato et al. | .................. | 203/73 |
| 4,828,652 | * | 5/1989 | Schropp | ..................... | 203/38 |
| 5,196,578 | * | 3/1993 | Kuragano et al. | ............. | 562/600 |
| 5,315,037 | * | 5/1994 | Sakamoto et al. | ............. | 562/600 |
| 5,482,597 | * | 1/1996 | Herbst et al. | ................ | 203/59 |
| 5,910,607 | * | 6/1999 | Sakakura et al. | ............. | 562/532 |

FOREIGN PATENT DOCUMENTS

| 551 111 A1 | 7/1983 | (EP) . |
| 0312191 | * 4/1989 | (EP) . |
| 49-21124 | 5/1974 | (JP) . |
| 252446 | * 12/1985 | (JP) . |
| 63-10691 | 3/1988 | (JP) . |
| 3-181440 | 8/1991 | (JP) . |
| 9-208515 | 8/1997 | (JP) . |

OTHER PUBLICATIONS

Patent Abstract of Japan, vol. 1997, No. (Dec. 25, 1997) & JP 09 208515 A (Idemitsu Petroche Co LTD), (Aug. 12, 1997)

Patent Abstracts of Japan, vol. 00, No. 125 (C–283), (May 30, 1985) & JP 60 013739 A (Sumitomo Kagaku Kogyo KK), (Jan. 24, 1985).

* cited by examiner

Primary Examiner—Virginia Manoharan
(74) Attorney, Agent, or Firm—Pillsbury Madison & Sutro LLP

(57) ABSTRACT

The present invention concerns a method for producing acrylic acid which involves subjecting an acrylic acid-containing aqueous solution obtained by catalytic vapor phase oxidation of propylene and/or acrolein to evaporation whereby an acrylic acid-containing vapor is obtained; and subjecting the acrylic acid-containing vapor to azeotropic dehydration. The present invention offers a number of advantages including a reduce amount of polymer that may adhere to the surface of an azeotropic dehydration column, a low-blowing separation column or an in a high-boiling separation column in a plant for producing acrylic acid. Consequently, the production plant can be operated for a long time without stopping operations.

3 Claims, No Drawings

METHOD FOR PRODUCING ACRYLIC ACID

BACKGROUND OF THE INVENTION

1. Field of the Invention

The present invention relates to a method for producing acrylic acid in which acrylic acid is separated from an acrylic acid-containing aqueous solution obtained by catalytic vapor phase oxidation of propylene and/or acrolein while preventing polymerization.

2. Description of the Related Art

Acrylic acid has currently been produced by catalytic vapor phase oxidation of propylene and/or acrolein in the industrial scale. Since catalytic oxidation is conducted with a solid catalyst in the presence of molecular state oxygen and water vapor, the oxidation product is usually obtained in the form of an acrylic acid-containing aqueous solution.

The acrylic acid-containing aqueous solution contains many by-products, other than acrylic acid, such as acetic acid, formic acid, formaldehyde, furfural, acrolein, acetaldehyde, propionic acid, maleic acid, benzaldehyde, protoanemonin and the like.

In order to recover acrylic acid from such acrylic acid-containing aqueous solution, it is necessary to first remove water from the acrylic acid-containing aqueous solution.

As the method for removing water from the acrylic acid-containing aqueous solution, the following methods have been known.

(1) Solvent extraction methods using a solvent such as a ketone, an acetic acid ester, a butyric acid ester, an aromatic hydrocarbon or the like (for example, Publication of Examined Japanese Patent Application No. Sho 46-18728, Publication of Examined Japanese Patent Application No. Sho 49-34966, Publication of Unexamined Japanese Patent Application No. Sho 48-62712, Publication of Unexamined Japanese Patent Application No. Sho 49-5915 and the like).

(2) Dehydration methods by azeotropic distillation using a solvent which boils azeotropically with water such as toluene, methyl isobutyl ketone and the like (for example, Publication of Unexamined Japanese Patent Application No. Sho 49-7216, Publication of Examined Japanese Patent Application No. Sho 63-10691, Publication of Unexamined Japanese Patent Application No. Hei 3-181440, Publication of Examined Japanese Patent Application No. Sho 41-11247 and the like).

In recent years, the dehydration method by azeotropic distillation has become the main current because of economic grounds and also of the fact that the concentration of acrylic acid in the acrylic acid-containing aqueous solution is remarkably increased up to 40 to 70% by weight and the concentration of water is remarkably decreased due to improvement in the performance of catalysts for catalytic vapor phase oxidation of propylene and/or acrolein and in the conditions for oxidation.

Since, however, acrylic acid has a property of easily polymerizing by the action of heat, light, peroxides, impurities such as aldehydes and so on, a large amount of polymers is produced when the acrylic acid-containing aqueous solution which contains many by-products is subjected to dehydration through azeotropic distillation by feeding directly to an azeotropic dehydration column. It is known that these polymers causes not only decrease in heat-transfer performance by adhering onto a heat surface of a reboiler for distillation column but also blockade of a distillation column leading to the situation including unwilled stop of operation. Therefore, prevention of the polymerization is very important from the industrial viewpoint.

As a means for preventing polymerization of acrylic acid, it has conventionally been proposed and conducted to add polymerization inhibitors to the acrylic acid-containing solution. As representative polymerization inhibitors are known phenols such as hydroquinone, hydroquinone monomethyl ether and the like, amines such as phenothiazine, diphenylamine and the like, copper salts such as copper dibutyldithiocarbamate and the like, manganese salts such as manganese acetate and the like, nitro compounds, nitroso compounds and so on. These polymerization inhibitors have been used independently or in combination with themselves or in combination with a molecular state oxygen-containing gas.

In addition, since the presence of impurities such as aldehydes has recently been deemed to be a problem in the case of producing a water absorptive resin and a polymeric coagulant in which the polymerization of acrylic acid is affected greatly by impurities, there have been proposed methods for purifying acrylic acid as follows;

(1) a method for purifying acrylic acid in which an aromatic amine, an aliphatic amine, or another amine such as an amide, an imine, an imide, a polyamine or the like is added to a crude aldehyde-containing acrylic acid and the mixture is distilled to remove aldehydes from acrylic acid (Publication of Examined Japanese Patent Application No. Sho 48-31087).

(2) a method for preventing polymerization of acrylic acid and/or a method for decomposing aldehydes contained in acrylic acid in which at least one compound selected from the group consisting of ammonia, methylamine, ethylamine, dimethylamine, diethylamine and salts thereof are added to acrylic acid obtained by catalytic vapor phase oxidation of propylene and/or acrolein (Publication of Unexamined Japanese Patent Application No. Sho 50-50314).

(3) a method for purifying acrylic acid in which acrylic acid obtained by catalytic vapor phase oxidation of propylene and/or acrolein is treated with a molecular sieve having an adsorbed hydrazine compound or an amine compound to decompose and remove aldehydes contained in acrylic acid (Publication of Unexamined Japanese Patent Application No. Sho 56-18934).

(4) a method for purifying acrylic acid in which a primary amine and/or a salt thereof and, in addition, at least one organic sulfonic acid and/or a salt thereof are added to acrylic acid containing aldehydes, and acrylic acid is separated from the mixture by distillation (Publication of Unexamined Japanese Patent Application No. Hei 7-149687).

(5) a method for producing acrylic acid in which, in the evaporative purification of acrylic acid with addition of a de-aldehyde agent after azeotropic dehydration of an oxidation product containing acrylic acid obtained by catalytic vapor phase oxidation of propylene and/or acrolein, at least one amine selected from aliphatic amines, heterocyclic amines and aromatic monoamines and a dealdehyde agent are added to the solution after azeotropic dehydration (Publication of Unexamined Japanese Patent Application No. Hei 9-208515).

These methods are designed to obtain acrylic acid containing less amount of aldehydes by distillation of a solution after adding an amine in order to remove a small amount of aldehydes contained in acrylic acid, or relate to a treatment of aldehyde-containing acrylic acid with a molecular sieve having an adsorbed amine compound. Problems arise, however, that polymerization is liable to occur in a distillation column and a tarry substance is produced during the distillation of aldehyde-containing acrylic acid with addition of amines.

In addition, the life of molecular sieve shortens when the treatment is conducted with a molecular sieve having an adsorbed amine compound.

SUMMARY OF THE INVENTION

An object of the present invention is to provide a method for producing acrylic acid which comprises subjecting an acrylic acid-containing aqueous solution obtained by catalytic vapor phase oxidation of propylene and/or acrolein to azeotropic dehydration to separate acrylic acid; the method enable to prevent polymerization in separation of acrylic acid, reduce adherence of polymers either to an azeotropic dehydration column for removing water from the acrylic acid-containing aqueous solution or to a low-boiling separation column for removing impurities such as acetic acid or the like contained in the obtained acrylic acid or to a high-boiling separation column for removing high-boiling impurities such as maleic acid or the like, and obtain stably acrylic acid as the commercial product without stopping operation for a long period.

Under such circumstances, the present inventors have conducted an extensive research on a method for producing acrylic acid which comprises subjecting an acrylic acid-containing aqueous solution obtained by catalytic vapor phase oxidation of propylene and/or acrolein to azeotropic dehydration to separate acrylic acid; the method enable to reduce polymeric substance adhered in an azeotropic dehydration column or a distillation column for removing impurities contained in acrylic acid. As the result, they have found the fact that the above problem can be solved by once evaporating the acrylic acid-containing aqueous solution and then feeding the obtained acrylic acid-containing vapor to an azeotropic dehydration column to effect azeotropic dehydration, not feeding the acrylic acid-containing aqueous solution directly to an azeotropic dehydration column.

Thus, the present invention provides a method for producing acrylic acid which comprises subjecting an acrylic acid-containing aqueous solution obtained by catalytic vapor phase oxidation of propylene and/or acrolein to azeotropic dehydration to separate acrylic acid, in which the acrylic acid-containing aqueous solution is subjected to evaporation before azeotropic dehydration and the obtained acrylic acid-containing vapor is subjected to azeotropic dehydration.

DETAILED DESCRIPTION OF THE INVENTION

An acrylic acid-containing aqueous solution obtained by catalytic vapor phase oxidation of propylene and/or acrolein used in the present invention, may be either one obtained by the single step oxidation or the two step oxidation of propylene, or further one obtained by the system wherein raw exhaust gas is directly circulated to a oxidation reactor or circulated to a oxidation reactor after burning itself.

When propylene and/or acrolein is subjected to catalytic vapor phase oxidation by molecular state oxygen in the presence of water vapor and a solid catalyst, various aldehydes and various organic acids are produced in addition to acrylic acid and water. The composition of the acrylic acid-containing aqueous solution depends on the kind of the catalyst used and reaction conditions, but usually includes about 40 to 70% by weight of acrylic acid, 20 to 56% by weight of water and 2 to 10% by weight of acetic acid.

The present invention is characterized in that the acrylic acid-containing aqueous solution is first subjected to evaporation with an evaporator and the obtained acrylic acid-containing vapor is subjected to azeotropic dehydration, and not subjecting the solution directly to azeotropic dehydration as seen in the conventional method. The type of the evaporator used in the present invention is not particularly limited but usually includes those of wet wall column system and of forced circulation system. The pressure for evaporation operation is not particularly limited but it is preferred to operate at a pressure somewhat higher than the operating pressure in the azeotropic dehydration column, because it is necessary to feed the generated vapor to the subsequent azeotropic dehydration column. The evaporator may either be single-stage or multi-stage. It is preferred to use a multi-stage evaporator in order to increase recovery of acrylic acid. The rate of evaporation is preferably at least 90%. It is desirable to recover acrylic acid by feeding the bottom residue in the evaporator to an acrylic acid recovering step such as dimer-degradation or the like.

In the operation for evaporation, it is preferred to add conventionally known polymerization inhibitors for acrylic acid including phenols such as hydroquinone, hydroquinone monomethyl ether and the like, amines such as phenothiazine, diphenylamine and the like, copper salts such as copper dibutyldithiocarbamate and the like, manganese salts such as manganese acetate and the like, nitro compounds, nitroso compounds and so on, and further to blow a gas containing molecular state oxygen.

In addition, in order to enhance the effect of the present invention, it is preferred to add at least one compound selected from the group consisting of ammonia, primary amines, secondary amines, hydrazines, urea or salts thereof to the acrylic acid-containing aqueous solution before the acrylic acid-containing aqueous solution is evaporated. Addition of triethylenetetramine is particularly preferred. The primary amines and secondary amines include aliphatic amines such as ethanolamine, diethanolamine, diethylamine, hexamethylenediamine, octylamine, triethylenetetramine, diethylenetriamine, propylamine, hexylamine, triethylenepentamine, tetraethylenepentamine, ethylenediamine and the like; alicyclic amines such as cyclohexylamine, cyclopentylamine and the like; and aromatic amines such as phenylenediamine and the like. The hydrazines include hydrazine, phenylhydrazine and the like.

When at least one compound selected from the group consisting of ammonia, primary amines, secondary amines, hydrazines, urea or salts thereof are added to the acrylic acid-containing aqueous solution, these compounds are added in an amount of about 10 to 1,000 ppm to the acrylic acid-containing aqueous solution. The temperature for addition is usually within a range of about 10 to 100° C. and preferably about 30 to 80° C. Further, the duration of contact is not particularly limited and usually about 5 to 150 minutes. The site of addition is not particularly limited and preferably the addition is in the bottom liquid in the absorption tower for a gas produced by catalytic vapor phase oxidation of propylene and/or acrolein, or in a tank for the acrylic acid-containing aqueous solution. The means for mixing may be one which allows sufficient mixing of the additives and the acrylic acid-containing aqueous solution and includes, for example, static mixer, line mixer, stirring machine, storage tank for acrylic acid-containing aqueous solution having a pump circulation line and the like.

Then, the obtained vapor of the acrylic acid-containing aqueous solution is fed to an azeotropic dehydration column in order to remove mainly water. The method for the treatment in the azeotropic dehydration column is not particularly limited and may be a conventional method used in the production of acrylic acid. For example, the azeotropic dehydration is carried out with toluene, methyl isobutyl ketone, xylene, ethylbenzene, heptane or a mixture thereof under a vacuum of about 100 to 200 mmHg. By treating in such azeotropic dehydration column, the water content of a solution at the bottom of the azeotropic dehydration column usually becomes to 1,000 ppm or lower. On the other hand, water, acetic acid, azeotropic agent and low-boiling aldehydes are distilled out from the top of the azeotropic dehydration column. It is preferred that water and the azeotropic agent are not mutually soluble. The aqueous phase of the distillate is withdrawn to outside of the system and the oily phase is returned to the azeotropic dehydration column as a reflux.

The bottom liquid withdrawn from the azeotropic dehydration column is then fed to a low-boiling separation column at which low-boiling substances such as water, acetic acid, azeotropic agent are removed. Acrylic acid as the commercial product is obtained from the bottom liquid in the low-boiling separation column after a further purification by distillation, if necessary. On the other hand, the distillate from the low-boiling separation column containing acrylic acid, azeotropic agent and acetic acid is further distilled to separate acetic acid and the remaining acrylic acid and azeotropic agent are fed back to preceding step such as the azeotropic dehydration column, low-boiling separation column or the like as an acrylic acid containing solution for recovery.

According to the conventional method in which acrylic acid-containing aqueous solution is directly fed to an azeotropic dehydration column for azeotropic dehydration, formation of polymers and tarry substances in the recovering region and in the reboiler of an azeotropic dehydration column are remarkable. Therefore, a stable operation for a long period is difficult. On the other hand, when an evaporation of acrylic acid-containing aqueous solution is conducted before an azeotoropic dehydration as in the present invention, adhering substance in the azeotropic dehydration column is remarkably reduced. Also, frequency of removing polymers adhered on complicated structures such as packed tower, sieve tray, heating surface of a reboiler as a heat supplying apparatus and the like is decreased. In addition, the evaporating apparatus has a simpler structure and is costless as compared with the distilling apparatus. Therefore, two series of evaporators may be placed for alternative use when polymeric substance adhered on the wall of the apparatus. In this case, the resting evaporation apparatus can be easily cleaned by washing with alkali or water jet washing. Furthermore, adhering substance in the low-boiling separation column for distilling the bottom liquid from the azeotropic dehydration column and in the high-boiling separation column can also be decreased. Therefore, the method has a great advantage for use in the industrial field.

EXAMPLES

The present invention will now be described in more detail with reference of Examples, which should not be construed as a limitation upon the scope of the present invention.

Example 1

Into a 2 $m^2$ wet-wall type evaporator was fed an acrylic acid-containing aqueous solution, obtained by two-step catalytic vapor phase oxidation of propylene, and containing 55% by weight of acrylic acid, 41% by weight of water, 3% by weight of acetic acid, and each several tens ppm to several thousands ppm of acrolein, formaldehyde, furfural, acetaldehyde, propionic acid, maleic acid, benzaldehyde, protoanemonin and so on as impurities, at a rate of 50 kg/hr, and heated with a saturated steam at 1.1 $kg/cm^2$. The generated vapor was fed to an azeotropic dehydration column. The system was designed such that the bottom liquid from the wet-wall type evaporator was circulated back to the evaporator with a pump except a part of the bottom liquid, which was withdrawn to outside with a pump. The air was supplied to the bottom of the evaporator at a rate of 0.3% by volume based on the boiled up vapor. Polymerization inhibitors were supplied to the evaporator so that the concentrations of hydroquinone and the concentration of copper dibutyldithiocarbamate were about 2,000 ppm and 100 ppm, respectively.

The azeotropic dehydration column used was made of stainless steel, had an inside diameter of 200 mm, packed with OP cascade mini-ring (manufactured by Dodwell & Company Ltd.) for a length of 5 m in the concentrating zone and 2 m in the recovering zone in the column, and equipped with a2 $m^2$ reboiler at the bottom of the column and a 4 $m^2$ condenser at the top of the column, with the outlet of the condenser being connected to a vacuum adjusting apparatus. The azeotropic agent was toluene, which was supplied from the reflux line so that the concentration of toluene in the bottom liquid was 17% by weight. The reboiler was heated with a saturated steam at 1.1 $kg/cm^2$ and adjustment of heating was controlled by the amount of steam. The distillate condensed by the condenser at the top of the column was phase-separated by standing in a decanter. The total amount of azeotropic agent phase was returned and an aqueous phase was withdrawn to outside of the system. The bottom liquid was withdrawn by a pump so that the liquid level was kept constant and used as a material for low-boiling separation column described later. In the azeotropic dehydration column, the pressure at the top of the column was controlled at 150 mm Hg. From the top of the column, phenothiazine and copper dibutyldithiocarbamate as the polymerization inhibitors were supplied so that the concentration thereof in the bottom liquid were about 200 ppm and 100 ppm, respectively. In addition the air was supplied to the reboiler at a rate of 0.3% by volume based on the boiled up vapor.

The operation of the evaporator and azeotropic dehydration column was continued in this manner for 23 days. The temperature at the top of the azeotropic dehydration column as this time was about 45° C. and the temperature at the bottom was about 80° C. The amount of the aqueous phase withdrawn from the decanter was 21 kg/hr and the aqueous phase had a composition containing 95% by weight of water, 4% by weight of acetic acid and 0.1% by weight of acrylic acid. The amount of the liquid withdrawn from the bottom of the azeotropic dehydration column was 31 kg/hr and the liquid contained 0.05% by weight of water, 2% by weight of acetic acid, 80% by weight of acrylic acid, 17% by weight of toluene, polymerization inhibitors and so on. The amount of the bottom liquid withdrawn from the evaporator was 3 kg/hr and the bottom liquid contained 10% by weight of water, 70% by weight of acrylic acid (including dimer), 4% by weight of acetic acid and high-boiling substances such as polymerization inhibitors. After continuously operating or 23 days, the operation of the evaporator and the azeotropic dehydration column was stopped and they were dismantled for inspection. Only a small amount of polymeric substance adhered at the inside surface of the evaporator and only a slight amount of black tarry substance adhered at the recovering zone.

The polymeric substance at each part was vacuum-dried at about 80° C. for 2 hours and measured the dry weight. The results of the measurement are shown in Table 1.

Then, the liquid withdrawn from the bottom of the azeotropic dehydration column was fed to the low-boiling separation column at a feeding rate of 300 g/hr to distillate and separate the low-boiling substance. The low-boiling separation column was a glass cylinder having an inside diameter of 30 mm, equipped with a 2 liter flask as a reboiler at the bottom and a condenser at the top of the column, with the outlet of the condenser being connected to a vacuum adjusting apparatus. The concentrating zone and the recovering zone of the low-boiling separation column were packed with stainless Dickson packing for a length of 15 cm and 60 cm, respectively. After supplying the distillate condensed in the condenser at the top of the column with polymerization inhibitors diluted with toluene so that the concentrations of phenothiazine and copper dibutyldithiocarbamate were about 200 ppm and 33 ppm, respectively, a part of the distillate was used as the reflux for the low-boiling separation column and the rest of the distillate was withdrawn to outside of the system. Heating of the flask acting as the reboiler was carried out with an oil bath and the amount of the distillate was adjusted by the temperature of the oil bath. The air was supplied to the bottom of the flask at a rate of 0.3% by volume based on the boiled up vapor. The liquid level in the flask was kept constant by withdrawing the bottom liquid from the flask by a pump. The operation of the low-boiling separation column was continued for 23 days controlling the pressure at the top of the column at 70 mmHg, the reflux ratio at 4, the temperature at the top of the column at about 63° C. and the temperature at the bottom of the column at about 82° C. The amount of the withdrawn distillate was 100 g/hr and the distillate had a composition containing 6% by weight of acetic acid, 40% by weight of acrylic acid and 54% by weight of toluene. The amount of the liquid withdrawn from the bottom of the low-boiling separation column was 200 g/hr and the liquid contained 98% by weight of acrylic acid, several ppm of toluene, 200 ppm of acetic acid, high-boiling substance, polymerization inhibitors and so on. After continuously operating for 23 days, the operation of the low-boiling separation column was stopped and it was dismantled for inspection. The weight of Dickson packing as the packing in the concentrating zone was increased by 0.35 g. The weight of the packing in the recovering zone was also increased by 0.35 g. Further, the weight of the flask as the reboiler was increased by 0.10 g. However, no visible production of polymer was observed at any zone.

Then, the liquid withdrawn from the bottom of the low-boiling separation column was fed to the high-boiling separation at a feeding rate of 400 g/hr to recover acrylic acid for the commercial product. The high-boiling separation column was a glass cylinder having an inside diameter of 30 mm, equipped with a 2 liter flask as a reboiler at the bottom and a condenser at the top of the column, with the outlet of the condenser being connected to a vacuum adjusting apparatus. The concentrating zone and the recovering zone of the high-boiling separation column were packed with stainless Dickson packing for a length of 30 cm and 10 cm, respectively. The distillate condensed in the condenser at the top of the column was supplied with phenothiazine so that the concentration was about 200 ppm. A part of the distillate was used as the reflux for the high-boiling separation column and the rest of the distillate was withdrawn as the product. Heating of the flask and the blowing of the air were carried out in the same manner as in the low-boiling separation column. The liquid level in the flask was kept constant by withdrawing the bottom liquid from the flask by a pump. The operation of the high-boiling separation column was continued for 10 days controlling the pressure at the top of the column at 75 mmHg, the reflux ratio at 1, the temperature at the top of the column at about 79 ° C. and the temperature at the bottom of the column at about 88° C.

The amount of the withdrawn distillate as the product from the high-boiling separation column was 350 g/hr and the distillate had a composition containing 99% by weight or more of acrylic acid, 0.1% or less of water, 300 ppm or less of acetic acid and, in addition, 100 ppm or less of aldehydes.

The amount of the liquid withdrawn from the bottom of the column was 50 g/hr and the liquid contained high-boiling substance, polymerization inhibitors and so on, in addition to acrylic acid. After continuously operating for 10 days, the operation of the high-boiling separation column was stopped and it was dismantled for inspection. The weight of Dickson packing as the packing in the concentrating zone was increased by 0.15 g. The weight of the packing in the recovering zone was also increased by 0.10 g. Further, the weight of the flask as the reboiler was increased by 0.13 g. However, no visible production of polymer was observed at any zone.

Example 2

The separation of acrylic acid was carried out in the same manner as in Example 1, except that 500 ppm of triethylenetetramine was added to the acrylic acid-containing aqueous solution.

The results are shown in Table 1.

Example 3

The separation of acrylic acid was carried out in the same manner as in Example 1, except that 500 ppm of diethylenetriamine was added to the acrylic acid-containing aqueous solution.

The results are shown in Table 1.

Comparative Example 1

The separation of acrylic acid was carried out in the same manner as in Example 1, except that the acrylic acid-containing solution was directly fed to the azeotropic dehydration column in the liquid form without passing through the evaporator.

The results are shown in Table 1.

TABLE 1

| | | Example 1 | Example 2 | Example 3 | Comparative Example 1 |
|---|---|---|---|---|---|
| Amount of polymer adhered in azeotropic dehydration column (g) | Reboiler | 0.80 | 0.29 | 0.48 | 3.60 |
| | Recovering zone | 64.4 | 54.2 | 55.9 | 146.9 |
| | Concentrating zone | 0.00 | 0.00 | 0.00 | 0.00 |
| Amount of polymer adhered in low-boiling separation column (g) | Bottom | 0.10 | 0.05 | 0.06 | 0.35 |
| | Recovering zone | 0.35 | 0.11 | 0.17 | 1.04 |
| | Concentrating zone | 0.35 | 0.11 | 0.11 | 1.04 |
| Amount of polymer adhered in high-boiling separation column (g) | Bottom | 0.13 | 0.03 | 0.05 | 0.40 |
| | Recovering zone | 0.10 | 0.05 | 0.05 | 0.25 |
| | Concentrating zone | 0.15 | 0.05 | 0.08 | 0.55 |

What is claimed is:

1. A method for producing acrylic acid which comprises subjecting an acrylic acid-containing aqueous solution obtained by catalytic vapor phase oxidation of propylene and/or acrolein to azeotropic dehydration to separate acrylic acid, in which at least one compound selected from the group consisting of primary and secondary amines are added to the acrylic acid-containing aqueous solution before the acrylic acid-containing aqueous solution is evaporated, the acrylic acid-containing aqueous solution is subjected to evaporation before said azeotropic dehydration whereby the obtained acrylic acid-containing vapor is subjected to said azeotropic dehydration.

2. The method for producing acrylic acid according to claim 1, wherein said at least one compound selected from the group consisting of primary and secondary amines is triethylenetetramine.

3. The method for producing acrylic acid according to claim 1, wherein said at least one compound selected from the group consisting of primary and secondary amines is diethylenetriamine.

* * * * *